United States Patent [19]

Argaud

[11] Patent Number: 4,963,360

[45] Date of Patent: Oct. 16, 1990

[54] EXOTHERMIC PACKAGE BODY HAVING A LAYER CONTAINING A MEDICINAL COMPONENT

[76] Inventor: Albert Argaud, 17 Bis, Rue Mansart, 78000 Versailles, France

[21] Appl. No.: 262,879

[22] Filed: Oct. 26, 1988

[30] Foreign Application Priority Data

Feb. 12, 1988 [JP] Japan .............................. 63-17062[U]

[51] Int. Cl.⁵ .............................................. A61F 2/00
[52] U.S. Cl. .................................... 424/443; 424/448; 424/445; 424/447
[58] Field of Search ................. 424/443, 447, 448, 449

[56] References Cited

U.S. PATENT DOCUMENTS

| | | | |
|---|---|---|---|
| 4,585,452 | 4/1986 | Sablotsky | 424/448 |
| 4,685,911 | 8/1987 | Konno et al. | 424/449 |
| 4,830,855 | 5/1989 | Stewart | 424/448 |

Primary Examiner—Merrell C. Cashion, Jr.
Assistant Examiner—Leon R. Horne
Attorney, Agent, or Firm—Wenderoth, Lind & Ponack

[57] ABSTRACT

An exothermic package body having a carrier layer comprising a medicinal component, and an exothermic layer which develops heat when exposed to the air to enhance absorption of the medicinal component through the skin, hence improving medicinal effects.

4 Claims, 1 Drawing Sheet

EXOTHERMIC PACKAGE BODY HAVING A LAYER CONTAINING A MEDICINAL COMPONENT

BACKGROUND OF THE INVENTION

1. Field of the Invention:

This invention relates to an exothermic package body which improves absorption of medicinal components through skin.

2. Description of the Related Art:

Hitherto, medicinal components to be absorbed through skin are commonly applied in the form of ointment applied onto skin or in the form of cataplasm agent. However, in these applications, for example, in case of the ointment, the problem exists that skin grows clammy and clothes are soiled.

Though, as for the medicinal components to be applied onto skin, the absorption performance is generally accelerated through warming by the body temperature, a method for improving the absorption performance has not yet been proposed.

In consideration of this state, the present invention provides an exothermic package body having a layer containing a medicinal component, which permits superior development of the effect of the medicinal component by improving the absorption of the medicinal component through skin.

SUMMARY OF THE INVENTION

The features of the exothermic package body having a layer containing a medicinal component according to the present invention exist in that an obverse surface of a base sheet is applied with a carrier layer composed of materials such as gelatin, cloth, and fibers which can absorb and hold a liquid comprising medicinal components such as marine algae essence, scopolamine, nitroglycerin, clonidine, and estradiol used for application onto skin, and a reverse surface of the base sheet has an exothermic body layer which develops heat through contact with air, and the above-described carrier layer is covered with a separable sheet, and the exothermic layer is covered with an air-permeable film and the base sheet together with the layers thereon is further sealed from exterior air and packed by an air-impermeable packing material.

DETAILED DESCRIPTION OF THE INVENTION

When a gelatin layer is used as the carrier layer, the well-known keratin simple protein for medical service can be used. The gelatin layer can be impregnated with medicinal components, e.g., marine algae essence by using propylene glycol (cosmetics material approved by the Welfare Ministry) as solvent. The above-described marine algae essence is well-known as a reducing drug. The carrier layer can comprise water, kaoline, aluminum chloride, antiseptics, or moisture absorbents, etc., besides the above-described medicinal components, and can further comprises a proper quantity of perfume, etc., and further the gelatin layer can comprises the essence of ivy, white birch, conkers, etc. which are well-known as medicinal components, together with or in substitution for the above-described medicinal components.

The above-described exothermic layer comprises well-known exothermic compositions (for example, mixture of iron powder, carbon, cellulose, resin, salt, and water, or $SiO_2$, silica, etc.), which develop an oxidation exothermic reaction through contact with air, and since the package body is applied directly onto skin, the exothermic compound is desirably selected from those which develop exothermic heat slightly higher than the body temperature, for example up to 45° C.

As the base sheet onto which the above-described carrier layer and exothermic layer are formed respectively on the obverse and reverse surfaces, a flexible sheet made of nylon, polyethylene, etc. can be used.

As the air-permeable film which covers the exothermic layer, nylon, polyethylene, etc. can be used, and as the substance for packing the whole, air-impermeable polypropylene, ethylene vinyl acetate, etc. can be used.

The present invention, with the above-described structure, permits application of the medicinal components onto skin in the same manner as the cataplasm agent and improves the absorption performance of the medicinal components through skin by the development of heat in the exothermic layer, and since the exothermic layer and the carrier layer comprising the medicinal components are separately structured, these layers can be constituted only from components which can meet with respective purposes, and the whole structure can be made simple.

DETAILED DESCRIPTION OF THE PREFERRED EMBODIMENTS

The present invention will be described with reference to the embodiment shown in the accompanying drawings.

Figure 1:
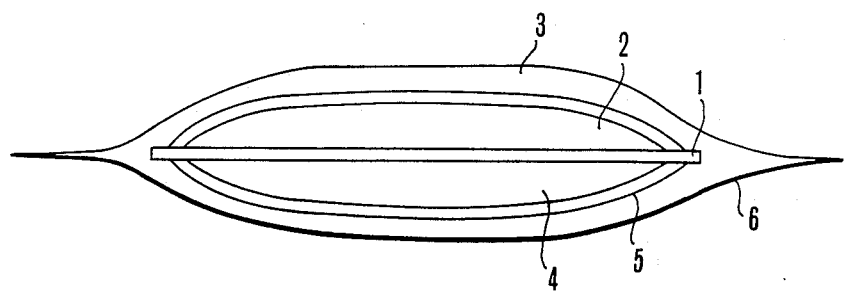
FIG. 1 and FIG. 2 show an example of the outline of the structure of an exothermic package body having a layer comprising a medicinal component according to the present invention.
Figure 2:
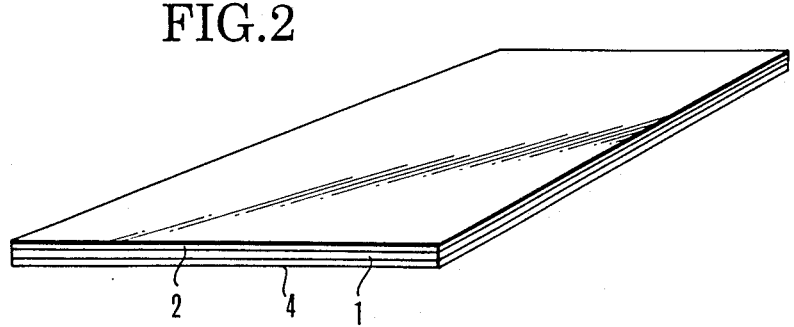

In FIGS. 1 and 2, 1 is a base sheet, 2 is a carrier layer such as a, gelatin layer formed on the observe surface of the base sheet, 3 is a cover film on the obverse surface, 4 is an exothermic layer formed on the reverse surface of the sheet 1, and the layer 4 is covered by an air-permeable cover film 5, and 6 is an air-impermeable packing material for packing the whole of the exothermic layer containing the medicinal component.

One example of the compositions of the exothermic layer and the carrier layer (gelatin layer) are set forth below. The gelatin layer is formed by mixing under agitation.

| Exothermic layer | |
|---|---|
| Iron powder | 10.0–14.0 g |
| Carbon powder | 1.0–2.0 g |
| NaCl (salt) | 0.5–1.0 g |
| Water | 3.5–5.5 g |
| $SiO_2$ | 1.0–2.0 g |
| Gelatin layer | |
| Water | 4.0–5.0 g |
| Gelatin | 1–2 g |
| Kaoline | 2–4 g |
| Antiseptics | 0.1–0.3 g |
| Aluminum chloride | 0.2–0.4 g |
| Propylene glycol containing essence | 0.1–0.3 g |

$SiO_2$ 1.5
Total 20.0 g Gelatin layer
Water 4.4 g

Gelatin, 1.3 g
.Caoline 2.8 g
Antiseptics 0.2 g
Aluminum chloride 0.3 g
Propylene glycol 1.0 g
containing essence
Total 10.0 g In the above, aluminum chloride is desirably added for suppressing perspiration.

Embodiment 1

An exothermic package body having an exothermic layer and a gelatin layer of the following composition was prepared.

| Exothermic layer | |
|---|---|
| Iron powder | 12.0 g |
| Carbon powder | 1.6 g |
| NaCl (salt) | 0.1 g |
| Water | 4.2 g |
| SiO$_2$ | 1.5 g |
| Total | 20.0 g |
| Gelatin layer | |
| Water | 4.4 g |
| Gelatin | 1.3 g |
| Kaoline | 2.8 g |
| Antiseptics | 0.2 g |
| Aluminum chloride | 0.3 g |
| Propylene glycol containing essence | 1.0 g |
| Total | 10.0 g |

In the above-described compositions, as the propylene glycol containing essence, use was made of a product (made by Gattefosse Co. (France); Trader, Sun Trade Co.) consisting of 0.6 g of marine algae essence, 0.2 g of Western ivy essence, 0.1 g of white birch essence and 0.1 g of Western conker essence.

In consideration of the present invention, the carrier layer comprising the medicinal components can be applied onto skin in a similar manner as the cataplasm agent, and the absorption performance of the medicinal component through skin by the development of heat due to the exothermic layer on the reverse surface can be improved, and since the exothermic layer and the carrier layer comprising the medicinal components are separatedly constituted, these layers can be composed only of the constituents suitable for the development of their desired effects, and selection of the mixed composition for these layers is facilitated.

What is claimed is:

1. An exothermic medical package body comprising:
   a base sheet;
   a carrier layer provided on an obverse surface of said base sheet, said carrier layer comprising 4.0–5.0 g of water, 1–2 g of gelatin, 2–4 g of kaoline, 0.1–0.3 g of antiseptic, 0.2–0.4 g of aluminum chloride, 0.1–0.3 g of propylene glycol, and a medicinal component;
   an exothermic layer, provided on a reverse surface of said base sheet, which develops heat when brought into contact with air;
   a separable cover for covering said carrier layer;
   an air-permeable film covering said exothermic layer, said film to be brought into contact with human skin to transmit heat of said exothermic layer to the skin; and
   an air-impermeable packing sheet for sealing and packing said exothermic layer covered by said film.

2. An exothermic medical package body according to claim 1, wherein said medicinal component is selected from the group consisting of marine algae essence, scopolamine, nitroglycerin, clonidine, and estradiol.

3. An exothermic medical package body comprising:
   a base sheet;
   a carrier layer provided on an obverse surface of said base sheet, said carrier layer comprising cloth or fibers impregnated with a medicinal component;
   an exothermic layer, provided on a reverse surface of said base sheet, which develops heat when brought into contact with air;
   a separable cover for covering said carrier layer;
   an air-permeable film covering said exothermic layer, said film to be brought into contact with human skin to transmit heat of said exothermic layer to the skin; and
   an air-impermeable packing sheet for sealing and packing said exothermic layer covered by said film.

4. An exothermic medical package body according to claim 3, wherein said medicinal component is selected from the group consisting of marine algae essence, scopolamine, nitroglycerin, clonidine, and estradiol.

* * * * *